US 6,733,469 B2

(12) United States Patent
Miyaji et al.

(10) Patent No.: US 6,733,469 B2
(45) Date of Patent: May 11, 2004

(54) CERVICAL VERTEBRAE ORTHOSIS

(75) Inventors: Yoshiki Miyaji, Kyoto (JP); Toru Nagano, Moriguchi (JP)

(73) Assignee: Nagano Prosthetics & Orthotics Co., Ltd. (JP)

( * ) Notice: Subject to any disclaimer, the term of this patent is extended or adjusted under 35 U.S.C. 154(b) by 97 days.

(21) Appl. No.: 10/123,171

(22) Filed: Apr. 17, 2002

(65) Prior Publication Data
US 2002/0173737 A1 Nov. 21, 2002

(30) Foreign Application Priority Data
May 21, 2001 (JP) ........................ 2001-150695

(51) Int. Cl.[7] .................................................. A61F 5/00
(52) U.S. Cl. ............................................ 602/18; 602/19
(58) Field of Search ..................... 128/845, DIG. 20; 602/16, 17, 18, 19

(56) References Cited
U.S. PATENT DOCUMENTS

| | | | | |
|---|---|---|---|---|
| 2,102,069 A | * | 12/1937 | Hanicke | |
| 4,194,501 A | * | 3/1980 | Watt | 128/DIG. 20 |
| 4,732,144 A | * | 3/1988 | Cunanan | 128/878 |
| 4,807,605 A | * | 2/1989 | Mattingly | 128/75 |
| 5,538,499 A | * | 7/1996 | Schwenn | 602/20 |
| 5,575,763 A | * | 11/1996 | Nagata | 602/1 |

FOREIGN PATENT DOCUMENTS
JP          2923559        7/1999

* cited by examiner

Primary Examiner—Michael A. Brown
(74) Attorney, Agent, or Firm—Bacon & Thomas, PLLC

(57) ABSTRACT

A cervical vertebrae orthosis. An angle of the orthosis can always be easily adjusted, rapidly and securely, and a lower jaw holding body and an occipital region holding body can always be supported stably. An angle adjusting device (53) of the cervical vertebrae orthosis is structured by coaxially pivoting a clutch member (54) with a radial pawl (56) fixed and attached to a thoracic cage body (1), a lower jaw holding body (6) and an occipital region holding body (8). A clutch portion (60) with a pawl (62) is formed in connection arms (51) and (52) so as to be engaged with the clutch member (54). A stopper ring (63) with an operation pawl (66) is attached to the connection arms (51) and (52) so as to engage the clutch member (54) with the clutch portion (60) and fix them. A holding member (76) with an operation pawl (80) is provided so as to engage with and press to operate the operation pawl (66) of the stopper ring (63).

1 Claim, 5 Drawing Sheets

CERVICAL VERTEBRAE ORTHOSIS

BACKGROUND OF THE INVENTION

1. Field of the Invention

The present invention relates to a cervical vertebrae orthosis, and more particularly to a cervical vertebrae orthosis which is attached to a human body so as to limit a motion of a troubled part in a portion between an upper portion of a thoracic vertebrae and cervical vertebrae, a skull bone and the like.

2. Description of the Conventional Art

In conventional, as this kind of cervical vertebrae orthosis, there has been known a cervical vertebrae orthosis previously disclosed by the inventor of the present application (Japanese Patent No. 2923559), and this will be described with reference to FIGS. 6 to 8.

That is, in the drawings, reference numeral 1 denotes a plastic thoracic cage body structured such as to be freely attached to a chest region of the human body, reference numerals 2 and 3 denote a front thoracic cage member and a rear thoracic cage member which constitute the thoracic cage body 1 and are formed in a substantially Y shape, reference numerals 4 and 5 denote a pair of attaching bands for shoulder and attaching bands for waist which are disposed in both sides and respectively fasten upper and lower portions of the front and rear thoracic cage members 2 and 3, reference numeral 6 denotes a lower jaw holding body which is mounted in a standing manner to the front thoracic cage member 2 via a pair of connection arms 7 in both sides, and reference numeral 8 denotes an occipital region holding body mounted in a standing manner to the rear thoracic cage member 3 via a pair of connection arms 9 in both sides. Reference numerals 10 and 11 denote an upper connection arm member and a lower connection arm member which respectively constitute the front connection arms 7 in both sides, have desired lengths and are formed in a substantially link piece shape, reference numeral 12 denotes a substantially plate-like joint member which movably connects free ends of the upper and lower connection arm members 10 and 11 by pivot pins 13, and reference numeral 14 denotes a desired number of angle adjusting holes which are formed on an outer peripheral edge of the joint member 12 around the respective pivot pins 13 at respective predetermined pitches on the same circumference. The structure is made such that not only a height of the lower jaw holding body 6 but also an angle of anteflexion and retroflexion can be freely adjusted by fixing free end sides of the upper and lower connection arm members 10 and 11 to the desired angle adjusting holes 14 via fastening screws 15.

Reference numerals 16 and 17 denotes an upper portion connection arm member and a lower portion connection arm member which respectively constitute the rear connection arms 9 in both sides, have desired lengths and are formed in a substantially link piece shape, and reference numeral 18 denotes a substantially plate-like joint member which movably connects free ends of the upper and lower portion connection arm members 16 and 17 by the pivot pins 13. Angle adjusting holes 19 are formed in an outer peripheral edge of the joint member 18 in the same manner as those of the joint member 12, and the structure is made such that it is possible to freely adjust angles for anteflexion and retroflexion in addition to the height of the occipital region holding body 8 by suitably fixing the free end sides of the upper and lower portion connection arm members 16 and 17 to the desired angle adjusting holes 19 via the fastening screws 15. Reference numeral 20 denotes a pair of attaching bands in both sides which fasten the lower jaw holding body 6 to the occipital region holding body 8, and reference numeral 21 denotes a desired-shaped pad member mounted to inner surfaces of the thoracic vertebrae body 1 and the lower jaw and occipital region holding bodies 6 and 8.

According to the conventional art structured in the manner mentioned above, the front portion thoracic cage member 2 and the rear portion thoracic cage member 3 are placed on the chest region of the human body in an outward fitting manner and then fastened to the chest region by the attaching bands 4 and 5. Thereafter, by suitably fixing the respective upper and lower portion connection arm members 10, 11, 16 and 17 constituting the respective connection arms 7 and 9 in the front and rear portions to the angle adjusting holes 14 and 19 of the respective joint members 12 and 18 via the fastening screws 15 while moving the respective upper and lower portion connection arm members 10, 11, 16 and 17 in a predetermined direction, the lower jaw holding body 6 and the occipital region holding body 8 are suitably adjusted not only in the respective desired heights but also in the angles with respect to the anteflexion and the retroflexion. Next, the attaching band 20 is fastened while the lower jaw holding body 6 and the occipital region holding body 8 are placed on the lower jaw and the occipital region respectively. Further, a lower jawbone region and an occipital tubercle region are supported by a pair of front portion connection arms 7 and rear portion connection arms 9 in both sides via the lower jaw holding body 6 and the occipital region holding body 8, whereby the angle limitation in the anteflexion, retroflexion, rotation and lateral fold of the cervical vertebrae, and a load applied to the cervical vertebrae due to a weight of the head region are preferably reduced.

In this case, according to the conventional art structured in the manner mentioned above, since the respective upper and lower portion connection arm members 10, 11, 16 and 17 constituting the respective connection arms 7 and 9 in the front and rear portions are suitably fixed to the angle adjusting holes 14 and 19 of the joint members 12 and 18 via the fastening screws 15 so as to adjust the lower jaw holding body 6 and the occipital region holding body 8 not only in the respective desired heights but also in the angles in the anteflexion and retroflexion directions, the angle adjusting operation is very troublesome and needs a lot of work, and further, not only it is impossible to suitably execute a fine adjustment but also it is hard to stably support the lower jaw holding body 6 and the occipital region holding body 8.

SUMMARY OF THE INVENTION

An object of the present invention is to provide a cervical vertebrae orthosis which can solve the problems in the conventional art mentioned above, can always easily, rapidly and securely adjust an angle, and can always stably support a lower jaw holding body and an occipital region holding body.

That is, in accordance with the present invention, there is provided a cervical vertebrae orthosis comprising:

a thoracic cage body 1 being freely attachable to a chest region of a human body in an outward fitting manner; and a lower jaw holding body 6 and an occipital region holding body 8 respectively mounted to front and rear of an upper portion in the thoracic cage body 1 via a pair of connection arms 51 and 52 with angle adjusting means 53 in both sides, wherein the angle adjusting means 53 is structured by coaxially pivoting a clutch member 54 with a radial pawl 56 fixed and attached to each of the thoracic cage body 1, the lower jaw holding body 6 and the occipital region holding body 8, a clutch portion 60 with the same shaped pawl 62 formed in the connection arms 51 and 52 so as to be engaged with the clutch member 54, a stopper ring 63 with an operation pawl 66 attached to the connection arms 51 and 52 so as to engage the clutch member 54 with the clutch portion 60 and fix them, and a holding member 76 with an operation pawl 80 provided so as to engage with and press to operate the operation pawl 66 of the stopper ring 63.

Then, in the cervical vertebrae orthosis in accordance with the present invention, the stopper ring 63 is rotated in a predetermined direction so as to cancel the engagement between the operation pawl 66 and the operation pawl 80 of the holding member 76 and cancel the engagement between the clutch member 54 and the clutch portion 60, the respective connection arms 51 and 52 are moved and adjusted to beat proper angles, then the clutch portion 60 is engaged with the clutch member 54, thereafter the stopper ring 63 is rotated in the predetermined direction so that the clutch portion 60 is pressed to the clutch member 54 to be fixed in an engagement state while the operation pawl 66 is engaged with the operation pawl 80 of the holding member 76, and thus the lower jaw holding body 6 and the occipital region holding body 8 can be properly adjusted not only in the suitable heights but also in the anteflexion and retroflexion directions.

DESCRIPTION OF THE PREFERRED EMBODIMENTS

A description will be given below of an embodiment in accordance with the present invention on the basis of one embodiment shown in the accompanying drawings.

Figure 1:
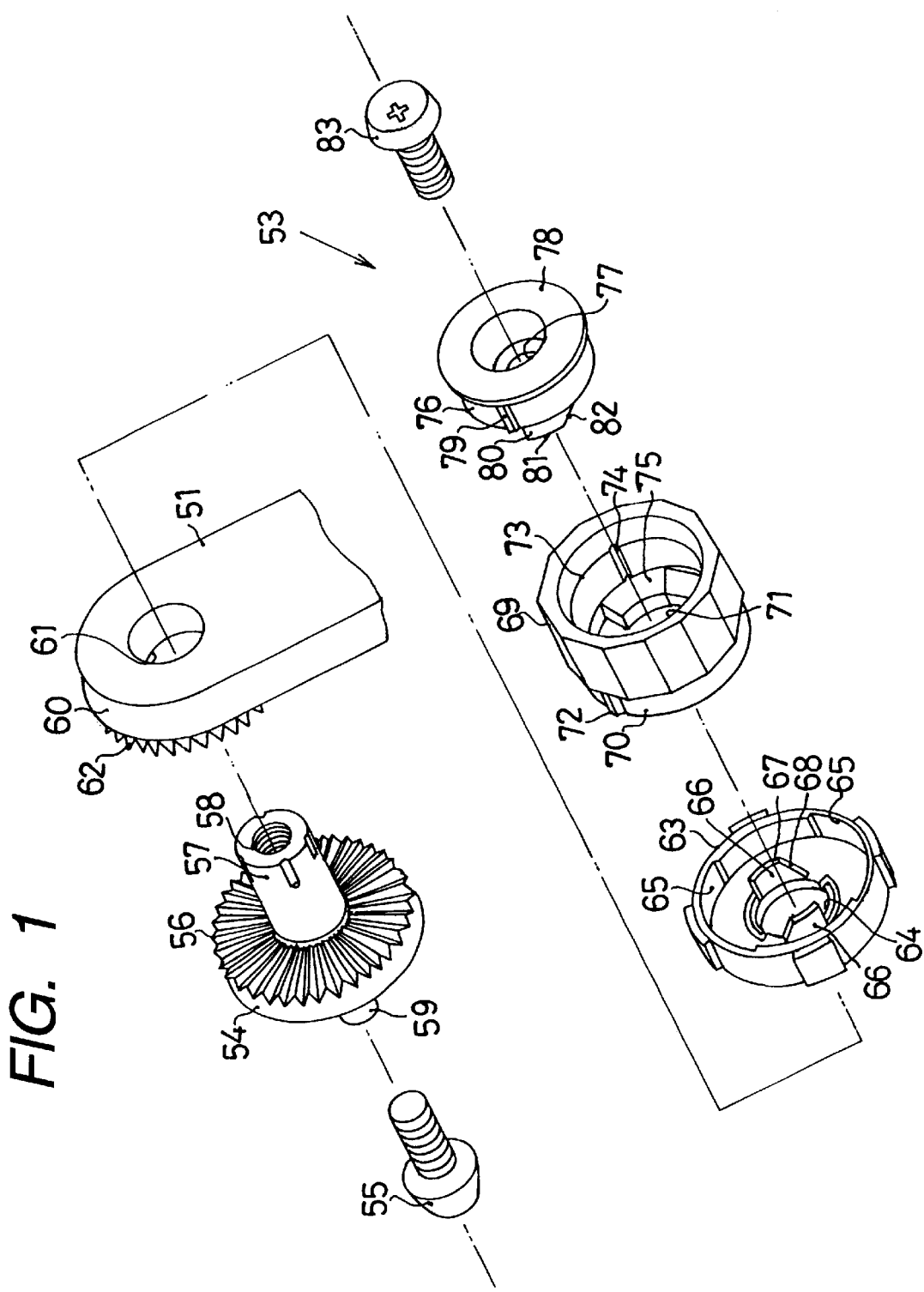
FIG. 1 is an exploded perspective view of a main portion showing one embodiment in accordance with the present invention.
Figure 2:
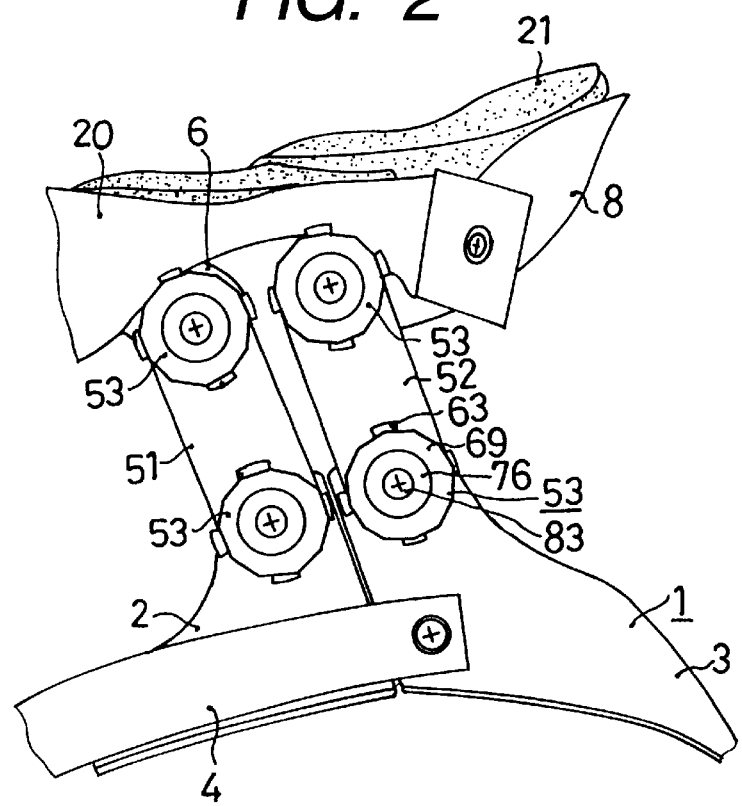
FIG. 2 is a partly enlarged side view showing an angle adjusting means 53 of the embodiment.
Figure 3:
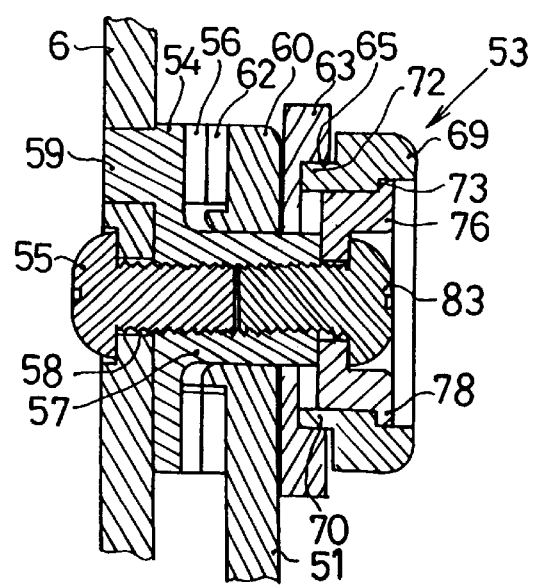
FIG. 3 is a vertical cross sectional view showing the angle adjusting means 53 of the embodiment.
Figure 4:
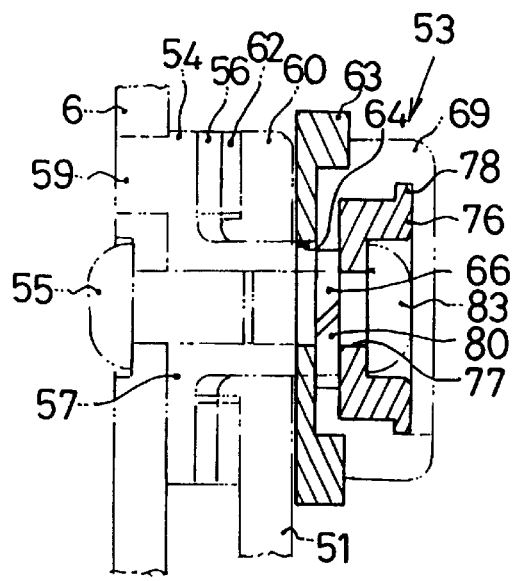
FIG. 4 is a vertical cross sectional view showing the state of canceling an engagement between an operation pawl 66 of a stopper ring 63 and an operation pawl 80 of a holding member 76 and canceling an engagement between a clutch member 54 and a clutch portion 60 in accordance with the embodiment.
Figure 5:
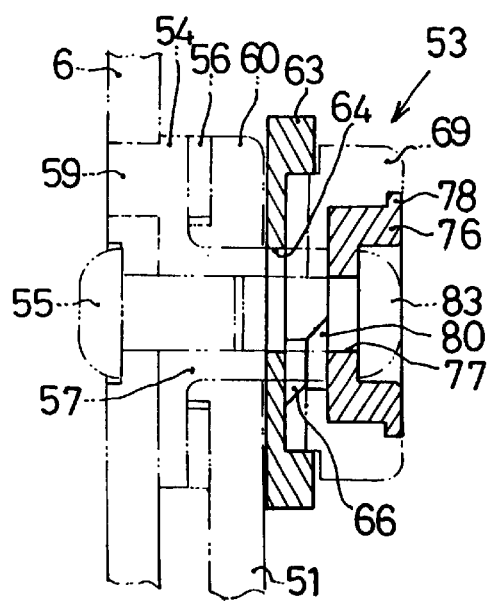
FIG. 5 is a vertical cross sectional view showing the state of engaging the operation pawl 66 of the stopper ring 63 with the operation pawl 80 of the holding member 76 and engaging the clutch member 54 and the clutch portion 60 so as to fix them in accordance with the embodiment.
Figure 6:
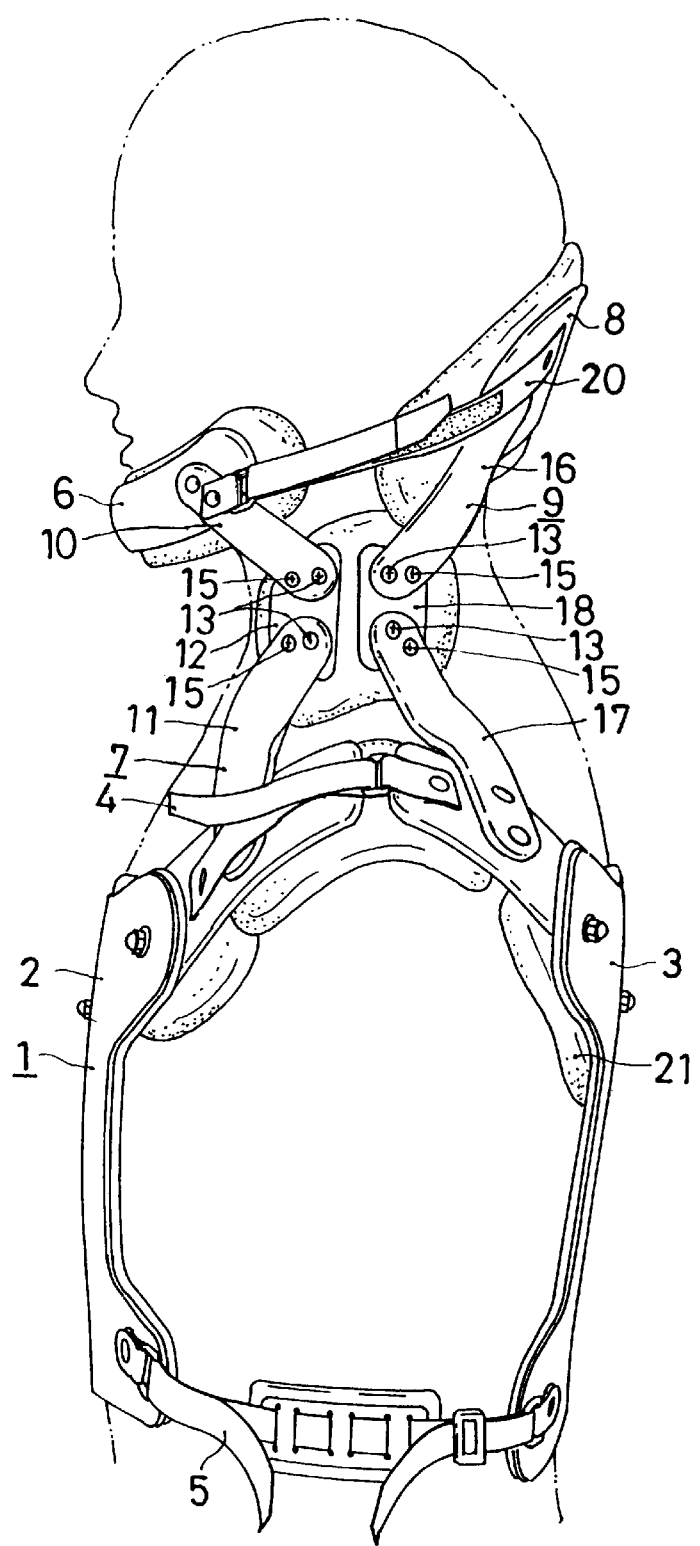
FIG. 6 is a side view showing a conventional art together with the state in use.
Figure 7:
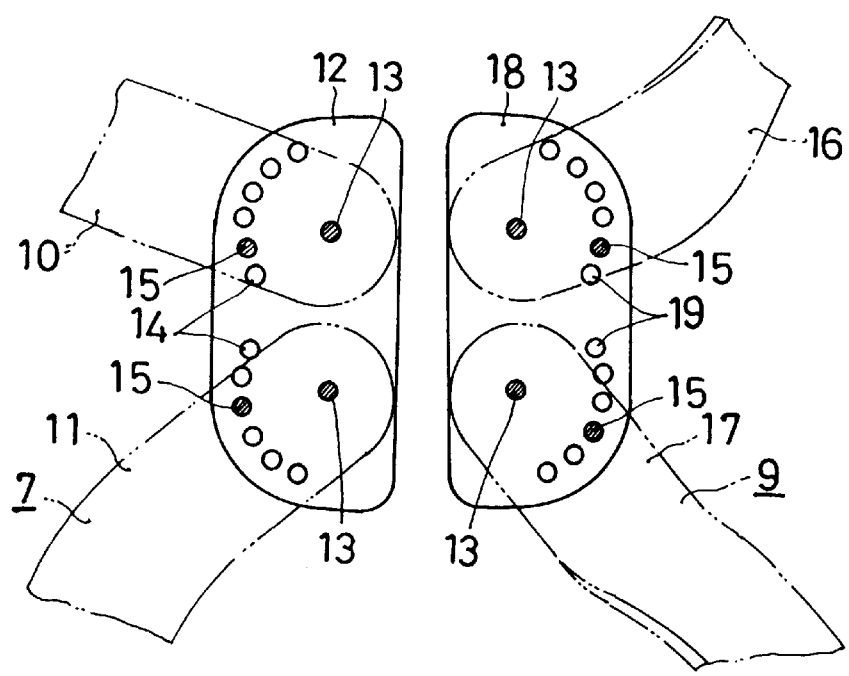
FIG. 7 is a partly enlarged side view showing an angle adjusting structure in accordance with a conventional art.
Figure 8:
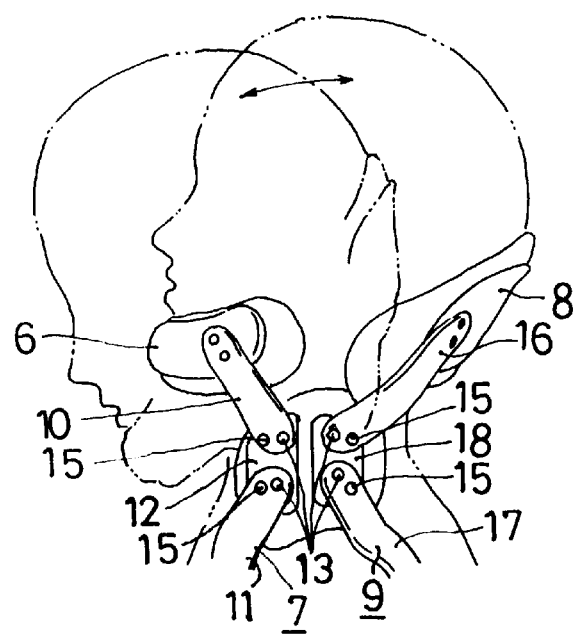
FIG. 8 is a side view showing the state of angle adjusting state of anteflexion and retroflexion in a lower jaw holding body 6 and an occipital region holding body 8 in accordance with the conventional art.

FIGS. 1 to 5 show one embodiment in accordance with the present invention. In the drawings, reference numerals 51 and 52 denote a pair of lower jaw holding body connection arms and occipital region holding body connection arms in both sides provided with desired widths and lengths so as to respectively connect an upper portion of a thoracic cage body 1 to a lower jaw holding body 6 and an occipital region holding body 8 via an angle adjusting means 53, and reference numeral 54 denotes a substantially bevel gear-shaped clutch member constituting the angle adjusting means 53. The clutch member 54 is fixed and attached to each of desired portions of the thoracic cage portion 1, the lower jaw holding body 6 and the occipital region holding body 8 via a fastening screws 55. Reference numeral 56 denotes a straight gear-shaped pawl of the clutch member 54 radially formed at a predetermined pitch, reference numeral 57 denotes a shaft with a threaded hole 58 having a desired length provided to protrude in a center of the clutch member 54, and reference numeral 59 denotes a mounting and positioning protruding piece protruding from a back surface of the clutch member 54. Reference numeral 60 denotes a clutch portion integrally formed in each of both end portions of each of the connection arms 51 and 52 so as to be coaxially engaged with the clutch member 54 via an axial hole 61, reference numeral 62 denotes a straight gear-shaped pawl having the same shape as that of the pawl 56 of the clutch member 54 formed in the clutch portion 60, reference numeral 63 denotes a substantially closed-end cylindrical stopper ring coaxially rotatably provided in both end portions of each of the connection arms 51 and 52 via an axial hole 64 so as to engage the clutch portion 60 with the clutch member 54 and fix them, reference numeral 65 denotes a pair of guide grooves in both sides formed in a notched shape on an inner peripheral wall surface of the stopper ring 63 with a desired width, and reference numeral 66 denotes a pair of operation pawls in both sides having a desired height and protruding on a bottom wall inner surface of the stopper ring 63 without opposing to the guide groove 65. The operation pawls 66 are positioned on the same circumference, and a flat surface portion 67 is formed in a top portion of each thereof, and an inclined surface portion 68 is formed in the same side in a symmetrical manner, respectively.

Reference numeral 69 denotes a closed-end cylindrical knob fitted to the stopper ring 63 via a fitting portion 70 and coaxially pivoted thereto via an axial hole 71, reference numeral 72 denotes a pair of guiding protrusion grooves in both sides protruded in an opposing manner on an outer peripheral surface along a center line direction of the fitting portion 70 so as to engage with the guide groove 65 and control the rotation of the stopper ring 63, reference numeral 73 denotes an engagement step portion formed stepwise on an inner peripheral wall surface of an upper end portion of the knob 69 so as to fit and engage a holding member 76 mentioned below, reference numeral 74 denotes an engagement groove formed on an inner peripheral wall surface of the knob 69 along a center line direction of the knob 69, and reference numeral 75 denotes a pair of engagement portions in both sides having desired heights and protruding on a bottom wall inner surface of the knob 69 so as to engage and hold an operation pawl 80 of the receiving member 76 mentioned below. The engagement portions 75 are positioned on the same circumference.

Reference numeral 76 denotes a closed-end cylindrical holding member coaxially fitted to the knob 69 via an axial hole 77, reference numeral 78 denotes an engaging flange formed in an outer end edge of the holding member 76 so as to be engaged with the engagement step portion 73 of the knob 69, reference numeral 79 denotes an engaging protrusion groove protruding on an outer peripheral surface of the holding member 76 along a center line direction of the holding member 76 so as to be engaged with the engagement groove 74, and reference numeral 80 denotes a pair of operation pawls in both sides protruding from a front end portion of the holding member 76 so as to be engaged with the operation pawl 66 of the stopper ring 63. The operation pawls 80 are positioned on the same circumference, and a flat surface 81 is formed in a top portion thereof and an inclined surface portion 82 is formed in a symmetrical manner in the same side, respectively. Further, an outer peripheral edge of the operation pawl 80 is engaged with and held in the engagement portion 75 of the knob 69. Reference numeral 83 denotes a fastening screw for a stopper engaged with the screw hole 58 of the shaft 57 through the axial hole 77 of the holding member 76. The operation pawls 66 and 80 can be property engaged by controlling of a movable width of the holding member 76 by the fastening screw 83. The other structures are the same as those of the conventional embodiment, and the same reference numerals denote the same portions.

Then, according to the embodiment structured in the manner mentioned above, similarly to the conventional one, the front portion thoracic cage member 2 and the rear portion thoracic cage member 3 are first placed on the chest region of the human body in an outward fitting manner and then fastened to the chest region by the attaching bands 4 and 5. Thereafter, the engagement between the operation pawl 66 of the stopper ring 63 and the operation pawl 80 of the holding member 76 is cancelled while each of the stopper rings 63 is rotated in the predetermined direction, and the engagement between the clutch member 54 and the clutch portion 60 is cancelled (refer to FIGS. 3 and 4). Next, the clutch portion 60 is engaged with the clutch member 54 after the respective connection arms 51 and 52 are adjusted to a desired angle while being moved in a predetermined direction. At this time, since the pawls 56 and 62 are radially formed in the clutch portion 60 and the clutch member 54 at the respective predetermined pitches, the respective connection arms 51 and 52 can be finely adjusted to a proper angle.

When the angle adjustment of each of the connection arms 51 and 52 is completed, the stopper ring 63 is rotated in the predetermined direction while the knob 69 is gripped so as to prevent the holding member 76 from rotating. At this time, the width of rotation of the stopper ring 63 is property controlled by the guiding protrusion 72 of the knob 69. Further, the clutch portion 60 is pressed to the clutch member 54 so as to be fixed engagedly while the operation pawl 66 of the stopper ring 63 is engaged with the operation pawl 80 of the holding member 76 due to the rotation of the stopper ring 63, and thereby the lower jaw holding body 6 and the occipital region holding body 8 are adjusted not only to the proper heights but also in the proper directions of anteflexion and retroflexion (refer to FIG. 5). Next, the fastening operation is executed via the attaching band 20 while the lower jaw holding body 6 is placed on the lower jaw of the human body and the occipital region holding body 8 is placed on the occipital region, respectively. Further, the structure is made such that the lower jawbone portion and the occipital tubercle region are supported by a pair of lower jaw holding body connection arm 51 and the occipital region holding body connection arm 52 in both sides via the lower jaw holding body 6 and the occipital region holding body 8, and thereby an angle limitation of the cervical vertebrae for anteflexion, retroflexion, rotation and lateral fold and a load applied to the cervical vertebrae by a weight of the head portion are properly reduced.

In this case, in the embodiment mentioned above, the pawls 56 and 62 of the clutch member 54 and the clutch portion 60 are respectively formed in the straight gear shape, however, may be formed in a bevel gear shape. Further, the holding member 76 is structured such as to be fitted to the knob 69, however, both of them may be integrally formed.

In accordance with the present invention, as mentioned above, since there is provided the cervical vertebrae orthosis comprising, the thoracic cage body 1 being freely attachable to the chest region of the human body in the outward fitting manner, and the lower jaw holding body 6 and the occipital region holding body 8 respectively mounted to front and rear of the upper portion in the thoracic cage body 1 via a pair of connection arms 51 and 52 with the angle adjusting means 53 in both sides, in which the angle adjusting means 53 is structured by coaxially pivoting the clutch member 54 with the radial pawl 56 fixed and attached to each of the thoracic cage body 1, the lower jaw holding body 6 and the occipital region holding body 8, the clutch portion 60 with the same shaped pawl 62 formed in the connection arms 51 and 52 so as to be engaged with the clutch member 54, the stopper ring 63 with the operation pawl 66 attached to the connection arms 51 and 52 so as to engage the clutch member 54 with the clutch portion 60 and fix them, and the holding member 76 with the operation pawl 80 provided so as to engage with and press to operate the operation pawl 66 of the stopper ring 63, it is possible to significantly easily, rapidly and securely adjust the angle in the directions of anteflexion and retroflexion in addition to the respective heights of the lower jaw holding body 6 and the occipital region holding body 8 by a significantly simple operation constituted by rotating the stopper ring 63 in the predetermined direction so as to cancel the engagement between the operation pawl 66 thereof and the operation pawl 80 of the holding member 76, canceling the engagement between the clutch member 54 and the clutch portion 60, adjusting the respective connection arms 51 and 52 to the proper angles while moving the respective arms 51 and 52, engaging the clutch portion 60 with the clutch member 54, and thereafter engaging and fixing the operation pawl 66 of the stopper ring 63 with the operation pawl 80 of the holding member 76 while rotating the stopper ring 63 in the predetermined direction. Further, it is possible to easily execute the fine adjustment on the basis of the engagement between the clutch member 54 and the clutch portion 60. Furthermore, since the connection arms 51 and 52 are respectively formed by the single members, it is possible to always stably support the lower jaw holding body 6 and the occipital region holding body 8 in comparison with the conventional example.

What is claimed is:

1. A cervical vertebrae orthosis comprising:
   a thoracic cage body (1) having left and right sides, said thoracic cage body (1) being freely attachable to a chest region of a human body in an outward fitting manner; and
   a lower jaw holding body (6) and an occipital region holding body (8) respectively mounted to front and rear of an upper portion in the thoracic cage body (1) via a pair of connection arms (51) and 52 with angle adjusting means (53) in the left and right sides of said thoracic cage body (1),
   wherein the angle adjusting means (53) is structured by coaxially pivoting a clutch member (54) with a radial pawl (56) fixed and attached to each of the thoracic cage body (1), the lower jaw holding body (6) and the occipital region holding body (8), a clutch portion (60) with a pawl (62) formed in each of the connection arms

(51) and (52) so as to be engaged with the clutch member (54), a stopper ring (63) with an operation pawl (66) attached to the connection arms (51) and (52) so as to engage the clutch member (54) with the clutch portion (60) and fix them, and a holding member (76) with an operation pawl (80) provided so as to engage with and press to operate the operation pawl (66) of the stopper ring (63).

* * * * *